United States Patent [19]

Neri et al.

[11] 4,447,544
[45] May 8, 1984

[54] METHOD AND REAGENT FOR DETERMINING INORGANIC PHOSPHATE IN BIOLOGICAL SAMPLE

[75] Inventors: Bruce P. Neri, North Andover; Stanley M. Liffmann, Methuen, both of Mass.

[73] Assignee: Instrumentation Laboratory Inc., Lexington, Mass.

[21] Appl. No.: 400,686

[22] Filed: Jul. 22, 1982

[51] Int. Cl.³ .................... G01N 33/52; G01N 33/84; G01N 33/96
[52] U.S. Cl. ..................................... 436/105; 436/19; 436/175
[58] Field of Search .................... 436/105, 175, 19

[56] References Cited

U.S. PATENT DOCUMENTS

| | | | |
|---|---|---|---|
| 3,771,961 | 11/1973 | Denney | 23/230 |
| 3,795,484 | 3/1974 | Daly et al. | 23/230 |
| 3,853,469 | 12/1974 | Morin et al. | 23/230 |
| 3,874,853 | 4/1975 | Byrnes | 23/230 |
| 3,920,580 | 11/1975 | Mast | 252/408 |
| 3,953,359 | 4/1976 | Gindler | 252/408 |
| 4,009,004 | 2/1977 | Hutchinson | 23/230 |
| 4,220,451 | 9/1980 | Stefanchik | 23/230 |

OTHER PUBLICATIONS

Chemical Abstracts, 94:188223, (1981).
John A. Daly, et al., "Direct Method for Determining Inorganic Phosphate in Serum with the 'Centrifi-Chem'", Clinical Chemistry, vol. 18, (1972), pp. 263-265.
Baadenhuijsen, et al., "Continuous–Flow Determination of Serum Inorganic Phosphate with a Single Reagent–The Vanadomolybdate Method Re-Evaluated", Clinical Chemistry, vol. 23, (1977), pp. 1275-1280.
Worthington, "Inorganic Phosphorus Reagent Set", Worthington Diagnostics, pp. 69-71, (1978).
Stanbio Laboratory Inc., "Fast (1 Min) Phosphorus Test", Set No. 0830, (1981).

*Primary Examiner*—Sidney Marantz

[57] ABSTRACT

An aqueous reagent for determining inorganic phosphate in a protein-containing liquid biological sample comprises a molybdate salt, an acid capable of reacting with the molybdate salt to form molybdic acid for complexation with phosphate to form phosphomolybdate complexes, a ferric salt in an amount sufficient to inhibit turbidity in the sample, and a nonionic surfactant reagent in an amount sufficient to further inhibit turbidity in the sample, the molybdate salt and the acid being present in amounts sufficient to form an amount of molybdic acid sufficient to produce a detectible color change when complexed with phosphate in the sample.

16 Claims, No Drawings

METHOD AND REAGENT FOR DETERMINING INORGANIC PHOSPHATE IN BIOLOGICAL SAMPLE

This invention relates to the quantitative determination of inorganic phosphorus in protein-containing biological fluids.

In such fluids, e.g. serum and urine, inorganic phosphorus, mainly in the form of phosphate, is measured using a molybdate salt such as ammonium molybdate and an acid such as sulphuric acid, which together form molybdic acid. The molybdic acid reacts with phosphate in the test sample to form phosphomolybdate complexes. Most methods further employ a reducing agent, e.g. stannous chloride or ferrous sulfate, which reduces the phosphomolybdate complex; the intensity of the blue color is then measured as a measure of inorganic phosphate in the sample.

It is also known to measure unreduced, yellow phosphomolybdate is a measure of phosphate. This provides the advantages of increased speed of analysis and avoidance of unstable reducing agents. One problem of such methods, however, is that the protein normally found in serum and urine tends to interact with the phosphomolybdate complex, causing turbidity which interferes with the colorimetric measurement.

The turbidity problem is partially alleviated by the sulphuric acid which is used to form the molybdic acid; an amount of acid sufficient to completely eliminate turbidity, however, has the undesirable effect of slowing the rate of phosphomolybdate formation. Detergents and surfactants such as Tween-80 have also been used to reduce turbidity, with some success. An additional compound which has been advantageously used in phosphate reagents is the accelerating and clarifying agent polyvinylpyrrolidone (PVP).

We have discovered that the addition of a ferric salt to a molybdic acid phosphate reagent reduces turbidity, allowing low amounts of acid to be used. The ferric salt-containing molybdic acid phosphate reagent provides very rapid (less than one minute) formation of colorimetrically measurable phosphomolybdate complexes.

Although the reason that a ferric salt can prevent turbidity even under low acid conditions has not been entirely elucidated, one explanation may be related to the behavior of the phosphomolybdate complex in an acidic environment. In such an environment, the complex may act as a strong acid, dissociating to form a negatively charged complex $(PMo_{12}O_{40})^{-3}$ which can complex with positively charged sites on protein molecules, causing turbidity. The prevention of turbidity by the presence of high concentrations of acid might be due to the acid's protonation, and thus neutralization, of the negatively charged phosphomolybdate complexes. In the absence of large concentrations of acid, the ferric $(Fe^{+3})$ ion may prevent turbidity by preventing protein/phosphomolybdate interaction, possibly by forming a heteropoly complex with the negatively charged phosphomolybdate complex.

The ferric salt should be used at a fairly low concentration since at 340 nm, the approximate wavelength used to detect yellow unreduced phosphomolybdate complexes, the ferric ion absorbs strongly, and thus produces high reagent blanks. Also, large concentrations of the ferric ion can interfere with phosphorus recovery and consequently can lower spectrophotometric readings for both blanks and serum samples.

Accordingly, the present invention features an aqueous reagent for determining inorganic phosphate in a protein-containing-liquid biological sample, the reagent including a molybdate salt, an acid capable of reacting with the molybdate salt to form molybdic acid for complexation with the phosphate in the sample to form colorimetrically measurable phosphomolybdate complexes, a ferric salt in an amount sufficient to inhibit turbidity in the sample, and a nonionic, low-phosphate surfactant in an amount sufficient to further inhibit turbidity in the sample. The molybdate salt and the acid are present in amounts sufficient to generate sufficient molybdic acid to produce a measurable color change when complexed with phosphate in the sample.

The preferred salt is ferric nitrate, the preferred molybdate salt is ammonium molybdate, the preferred acid is sulphuric acid, and the preferred surfactant is a mixture of Tween 80 and Igepal Ca 630A. Ammonium molybdate is preferably present in a concentration of between 0.60 mM and 2.40 mM, sulphuric acid is preferably present in a concentration of between 0.25 M and 0.72 M, the surfactant mixture is preferably present in a concentration of between 0.2% and 15%, v/v, and ferric nirate is preferably present in a concentration of between 0.2 mM and 1.2 mM.

In another aspect the invention features a serum-free, aqueous, inorganic phosphate standard solution containing inorganic phosphate and PVP. We have discovered that the PVP acts like protein in the standard, particularly as it affects viscosity, and thus provides very accurate standard phosphate colorimetric readings for comparison with protein-containing sample readings.

The ferric salt-containing reagents of the invention are useful in conjunction with a centrifugal automatic analyzer, e.g. the Instrumentation Laboratory MULTI-STAT ™ MCA analyzer, as well as with other types of analyzers. Such centrifugal analyzers advantageously use minimal amounts of reagents and also allow numerous samples to be analyzed simultaneously.

The IL MCA analyzer contains twenty radially arranged cuvettes, 19 of which contain samples, e.g. serum or urine, in sample cavities adjacent reagent wells containing the ferric salt-containing reagent. The 20th cuvette contains a water reference. When the rotor spins, reagent moves outward and mixes with sample. The samples are analyzed colorimetrically in the analyzer using double beam spectrophotometry, whereby the absorbances of the samples and the water reference are measured and compared as they spin past a fixed light beam.

The invention provides an improved reagent for analysis of the phosphate content of protein containing biological fluids that significantly reduces turbidity caused by the presence of the protein, without increasing reaction time. Other features and advantages will be seen as the following description of a particular embodiment that is illustrative of the invention progresses.

Two reagents, a color reagent and a surfactant reagent, are prepared and stored in separate containers. Just before use, the two reagents are combined in a 1:1 volume to make the working reagent which is combined with human blood serum samples. The two reagents are mixed less than 24 hours before use because the working reagent is stable for only about 24 hours.

The color reagent is formulated to contain, in a 1-liter aqueous solution, the following ingredients.

| Color Reagent | Range | Preferred |
| --- | --- | --- |
| Ammonium molybdate | 0.60mM–2.40mM | 1.21mM |
| Sulphuric acid | 0.25M–0.72M | 0.36M |
| $Fe(NO_3)_3$—$9H_2O$ | 0.2mM–1.2mM | 0.62mM |

A surfactant reagent is formulated to contain, in a 1-liter aqueous solution, the following ingredients.

| Surfactant Reagent | Range | Preferred |
| --- | --- | --- |
| Tween 80 | 3–20 ml/L | 12 ml/L |
| Igepal Ca 630A | 2–10 ml/L | 6 ml/L |
| Sodium Azide | | 0.5 g/L |

An inorgranic phosphate standard is formulated to contain, in a 1-liter aqueous solution, the following ingredients:

| Standard | Range | Preferred |
| --- | --- | --- |
| $KH_2PO_4$ | | 1.936m mol/L |
| Sulphuric acid | | 45 mol/L |
| PVP-40 | 2–6 g/L | 3 g/L |

The working reagent is used in conjunction with an IL MCA analyzer which includes 20 cuvettes, each comprising a sample cavity and a reagent cavity. Each sample cavity of seventeen of the cuvettes is loaded with a three microliter sample of human blood serum in 37 microliters of reagent grade water. The sample cavity of one of the cuvettes is loaded with 40 microliters of reagent grade water, and each sample cavity of the remaining two cuvettes is loaded with three microliters of the above-described phosphate standard in 37 microliters of reagent grade water (giving a phosphate concentration in the two standard sample cavities of 60 mg/L). The reagent cavity of each cuvette is loaded with 100 microliters of the above-described working reagent in 10 microliters reagent grade water.

The cuvette rotor is spun for three seconds and then stopped to mix the samples and reagents. After sixty seconds of further spinning (1,000 rpm), an initial reading in all cuvettes is taken at 380 nm wavelength to provide a sample blank reading which is a measure of cuvette variations and turbidity due to factors such as sample characteristics and serum-reagent interactions, and not phosphate, in the seventeen sample and two standard cuvettes. The interference filter is then shifted to provide readings at 340 nm, the wavelength corresponding to the yellow, unreduced phosphomolybdate complex. Fourteen readings are taken on each sample and standard at 1,000 rpm, 340 nm, and the values averaged. The change in absorbancy of the samples, between the 380 nm reading and the 340 nm reading, compared to the change in absorbancy for the standards, provides a rapid and precise measure of inorganic phosphate in the samples.

While a particular embodiment of the invention has been described, modifications thereof will be apparent to those skilled in the art, and therefore, it is not intended that the invention be limited to the particular embodiment or to details thereof and departures may be made therefrom within the spirit and scope of the invention.

What is claimed is:

1. An aqueous reagent for determining inorganic phosphate in a protein-containing liquid biological sample comprising
    a molybdate salt,
    an acid capable of reacting with said molybdate salt to form molybdic acid for complexation with said phosphate to form phosphomolybdate complexes,
    a ferric salt in an amount sufficient to inhibit turbidity in the sample, and
    a nonionic surfactant reagent in an amount sufficient to further inhibit turbidity in the sample,
    said molybdate salt and said acid being present in amounts sufficient to form an amount of molybdic acid sufficient to produce a detectible color change when complexed with said phosphate in said sample.

2. The aqueous reagent of claim 1 wherein said ferric salt is ferric nitrate.

3. The aqueous reagent of claim 2 wherein
    said ferric nitrate is present in a concentration of between 0.2 and 1.2 mM.

4. The aqueous reagent of claim 3 wherein said first nitrate is present in a concentration of about 0.62 mM.

5. The aqueous reagent of claim 1 wherein
    said molybdate salt is ammonium molybdate,
    said acid in sulphuric acid, and
    said ferric salt is ferric nitrate.

6. The reagent of claim 5 wherein
    said ammonium molybdate is present in a concentration of between 0.60 mM and 2.40 mM,
    said sulphuric acid is present in a concentration of between 0.25 M and 0.72 M, and
    said ferric nitrate is present in a concentration of between 0.2 mM and 1.2 mM.

7. A method of determining inorganic phosphate in a protein-containing liquid biological sample, said method comprising
    mixing said sample with an aqueous reagent comprising a molybdate salt, an acid, a nonionic surfactant, and a ferric salt to form colorimetrically detectable phosphomolybdate complexes while inhibiting the formation of turbidity-causing complexes of said protein with said phosphomolybdate complexes, and
    colorimetrically measuring said phosphomolybdate complexes as a measure of said inorganic phospate in said sample.

8. The method of claim 7 wherein said colorimetric measurement step includes a sample blank measurement at a first wavelength and a sample measurement at a second wavelength.

9. The method of claim 8 wherein said colorimetric measurement step is performed within about one minute of said mixing step.

10. The method of claim 9 wherein said sample is human blood serum.

11. A serum-free, aqueous inorganic phosphate standard solution for use in conjunction with a method in which the amount of phosphate in a protein-containing biological fluid sample is determined, said standard solution comprising
    a predetermined amount of phospate, and
    polyvinylpyrrolidone, in an amount ranging between 2 and 6 grams per liter of said standard solution.

12. An aqueous reagent for determining inorganic phosphate in a protein-containing liquid biological sample comprising a molybdate salt, an acid capable of reacting with said molybdate salt to form molybdic acid for complexation with said phosphate to form an unreduced phosphomolybdate complex, a ferric salt in an amount sufficient to inhibit turbidity in the sample, and a nonionic surfactant reagent in an amount sufficient to further inhibit turbidity in the sample, said molybdate salt and said acid being present in amounts sufficient to form an amount of molybdic acid with, when complexed with phosphate in said sample, forms an unreduced phosphomolybdate complex that has a detectable color that is a function of the phosphate in said sample.

13. The aqueous reagent of claim 12 wherein said ferric salt is ferric nitrate present in a concentration between 0.2 and 1.2 mM.

14. A method of determining inorganic phosphate in a protein-containing liquid biological sample, said method comprising mixing said sample with an aqueous reagent comprising a molybdate salt, an acid, a nonionic surfactant, and a ferric salt to form unreduced colorimetrically detectable phosphomolybdate complexes while inhibiting the formation of turbidity-causing complexes of said protein with said phosphomolybdate complexes, and colorimetrically measuring said unreduced phosphomolybdate complexes as a measure of said inorganic phosphate in said sample.

15. The method of claim 14 wherein said color measurement step includes a sample blank measurement at a first wavelength significantly offset from 340 nanometers and a sample measurement at about 340 nanometers.

16. The method of claim 14 wherein said sample is human blood serum and said colorimetric measurement step is performed within about one minute of said mixing step.

* * * * *

UNITED STATES PATENT AND TRADEMARK OFFICE
CERTIFICATE OF CORRECTION

PATENT NO. : 4,447,544

DATED : May 8, 1984

INVENTOR(S) : Bruce P. Neri et al.

It is certified that error appears in the above-identified patent and that said Letters Patent are hereby corrected as shown below:

Column 2, line 26, "nirate" should read --nitrate--.

Column 4, line 23, "first" should read --ferric--.

Column 5, line 15, "acid with" should read --acid which--.

Signed and Sealed this

Sixteenth Day of October 1984

[SEAL]

Attest:

GERALD J. MOSSINGHOFF

Attesting Officer

Commissioner of Patents and Trademarks